United States Patent
Berg et al.

[11] Patent Number: 5,897,537
[45] Date of Patent: *Apr. 27, 1999

[54] GUIDE CATHETER HAVING A PLURALITY OF FILLED DISTAL GROOVES

[75] Inventors: Todd A. Berg, Lino Lakes; Brian J. Scovil, Champlin; Jason A. Galdonik, Bloomington, all of Minn.

[73] Assignee: SciMed Life Systems, Inc., Maple Grove, Minn.

[*] Notice: This patent is subject to a terminal disclaimer.

[21] Appl. No.: 08/703,635

[22] Filed: Aug. 27, 1996

Related U.S. Application Data

[63] Continuation-in-part of application No. 08/195,222, Feb. 14, 1994, Pat. No. 5,569,218.

[51] Int. Cl.$^6$ ................................................. A61M 25/00
[52] U.S. Cl. ........................... 604/282; 604/280; 604/264; 138/134; 138/138
[58] Field of Search .................................. 604/280, 264, 604/281, 282; 138/123–125, 137–139, 140, 141, 153, 143–145

[56] References Cited

U.S. PATENT DOCUMENTS

| | | |
|---|---|---|
| 3,416,531 | 12/1968 | Edwards . |
| 3,485,234 | 12/1969 | Stevens . |
| 4,385,635 | 5/1983 | Ruiz . |
| 4,636,346 | 1/1987 | Gold et al. . |
| 4,690,175 | 9/1987 | Ouchi et al. . |
| 4,735,620 | 4/1988 | Ruiz ........................................ 604/281 |
| 4,838,879 | 6/1989 | Tanabe et al. . |
| 4,863,442 | 9/1989 | DeMello et al. ......................... 604/282 |
| 5,163,431 | 11/1992 | Griep ....................................... 604/282 |
| 5,176,660 | 1/1993 | Truckai ................................... 604/282 |
| 5,180,376 | 1/1993 | Fischell .................................. 604/282 |
| 5,221,270 | 6/1993 | Parker ..................................... 604/282 |
| 5,222,949 | 6/1993 | Kaldany ................................... 604/282 |
| 5,234,416 | 8/1993 | Macaulay et al. ....................... 604/282 |
| 5,254,107 | 10/1993 | Soltesz ................................... 604/282 |
| 5,279,596 | 1/1994 | Castaneda et al. ..................... 604/282 |
| 5,308,342 | 5/1994 | Sepetka et al. ......................... 604/282 |
| 5,358,493 | 10/1994 | Schweich, Jr. et al. ................ 604/264 |
| 5,423,774 | 6/1995 | Fischell et al. ......................... 604/282 |
| 5,509,910 | 4/1996 | Lunn ....................................... 604/280 |
| 5,514,108 | 5/1996 | Stevens .................................. 604/280 |
| 5,596,218 | 1/1997 | Berg ........................................ 604/282 |
| 5,599,319 | 2/1997 | Stevens .................................. 604/264 |

FOREIGN PATENT DOCUMENTS

| | | |
|---|---|---|
| 0 180 348 B1 | 5/1986 | European Pat. Off. . |
| 0 555 088 A2 | 8/1993 | European Pat. Off. . |
| 0 555 088 A3 | 8/1993 | European Pat. Off. . |
| WO 92/15356 | 9/1992 | WIPO . |

*Primary Examiner*—Ronald Stright
*Attorney, Agent, or Firm*—Crompton, Seager & Tufte, LLC

[57] ABSTRACT

A guiding catheter for use in coronary angioplasty and other cardiovascular interventions which incorporates a transition element in the shaft of the device. The transition element which has a different flexibility than the sections immediately proximal and distal to it, creates a zone in the catheter shaft which is either more or less flexible than the rest of the shaft. The transition element allows a portion of the shaft to be made more rigid or more flexible, without changing the flexibility of the other portions of the shaft. The transition element also allows for a differential flexibility to be added to the catheter shaft.

21 Claims, 14 Drawing Sheets

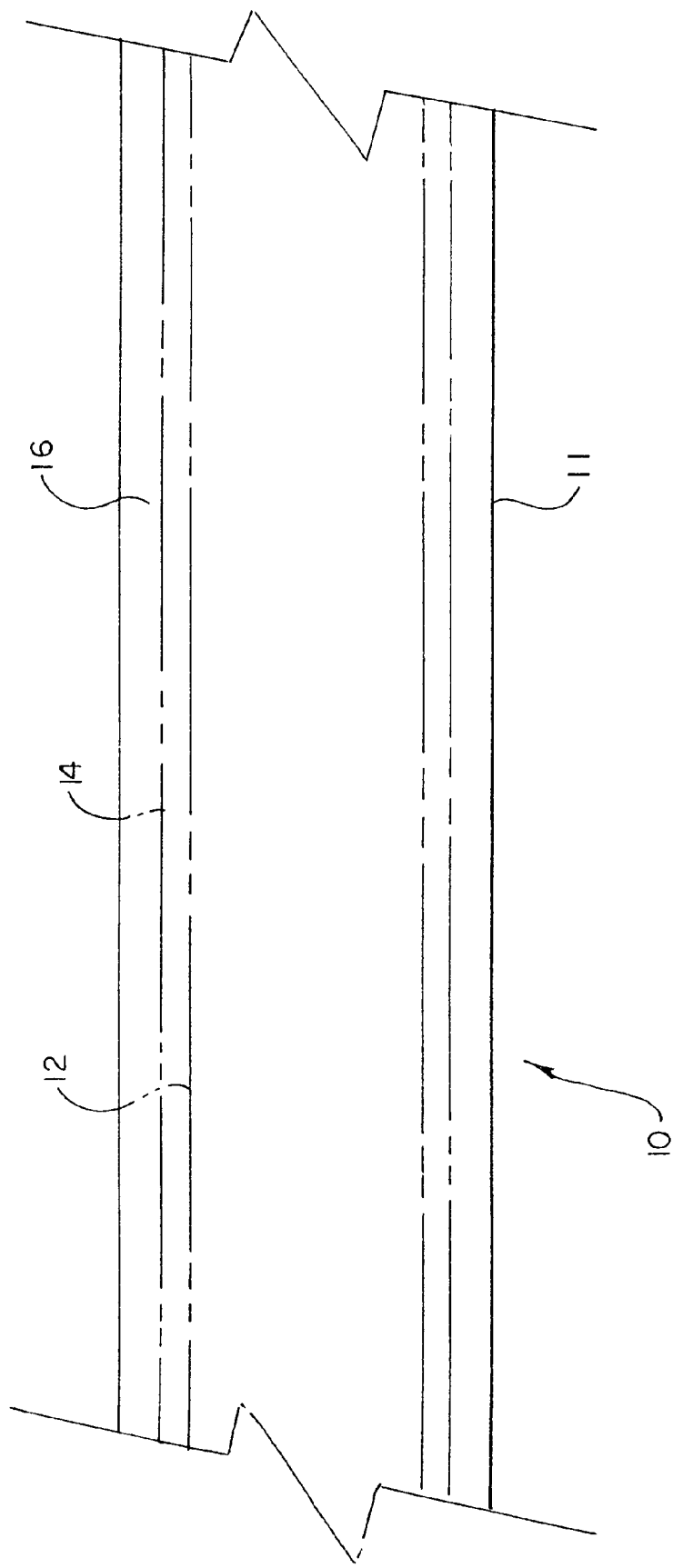

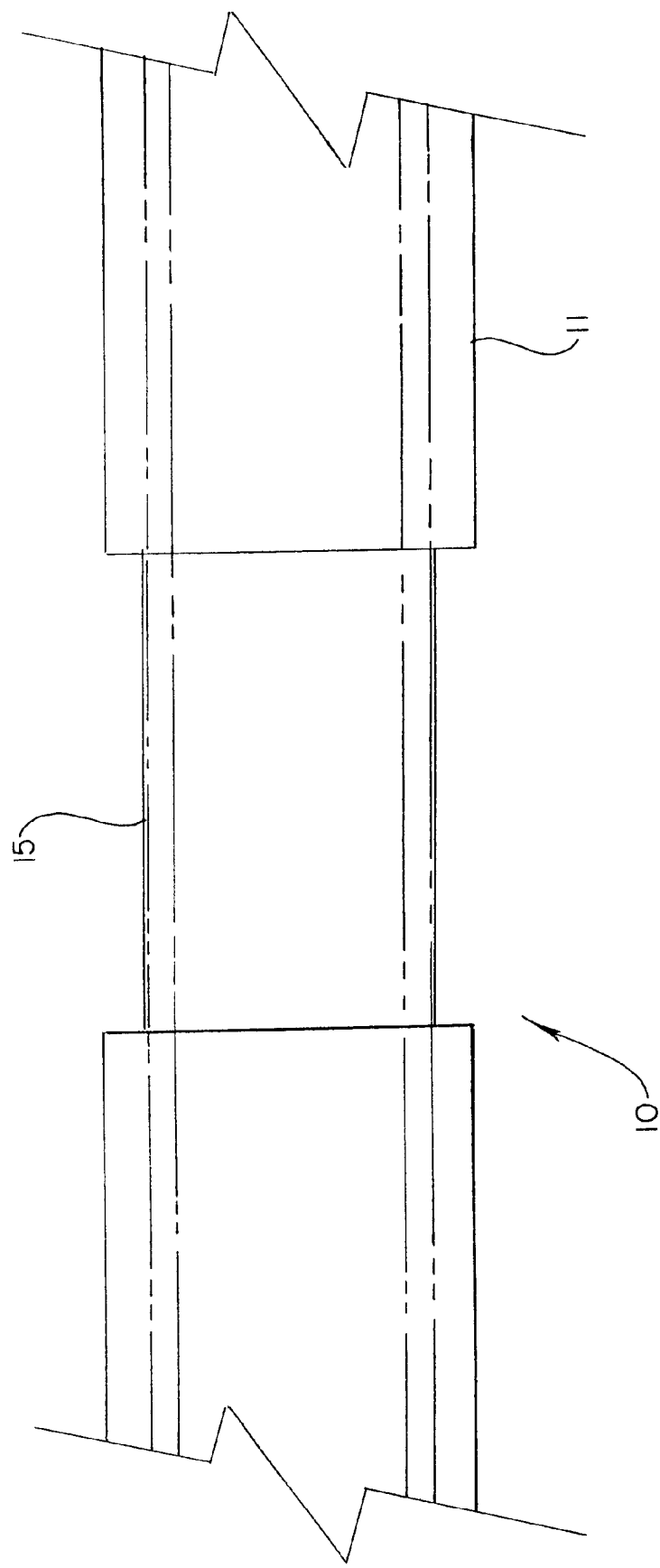

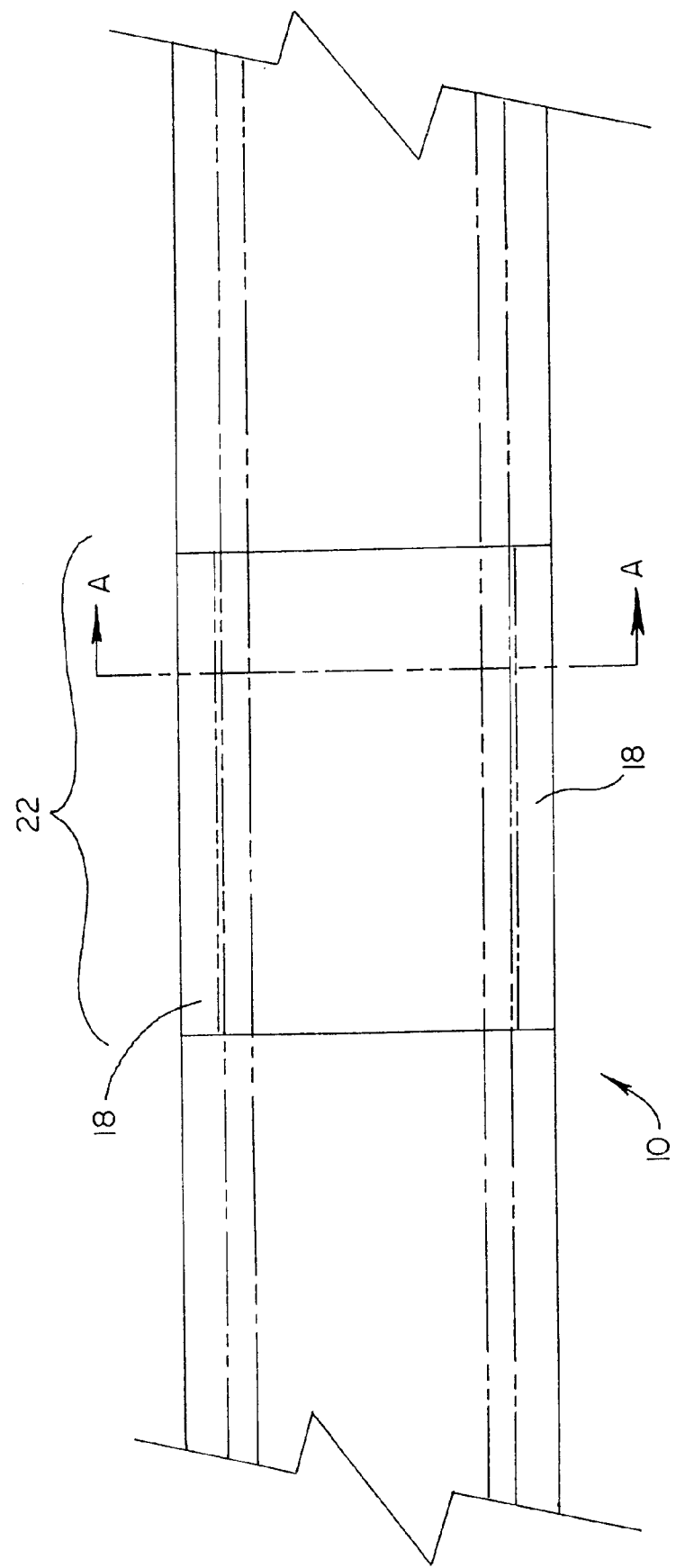

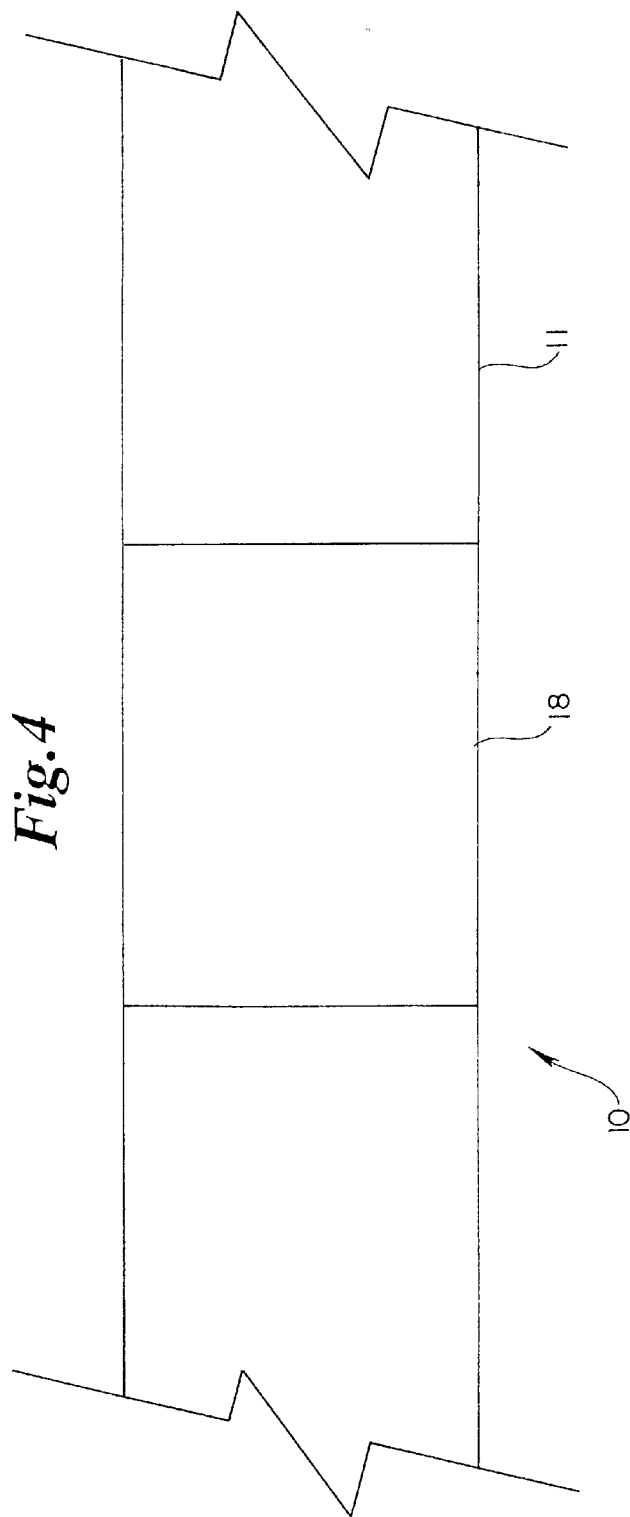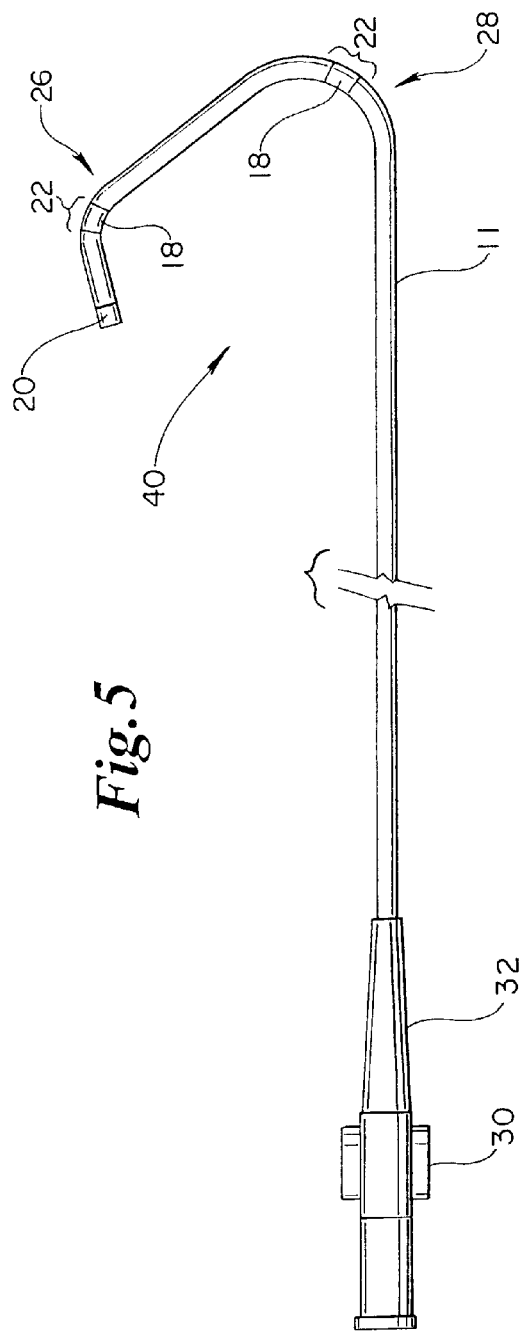

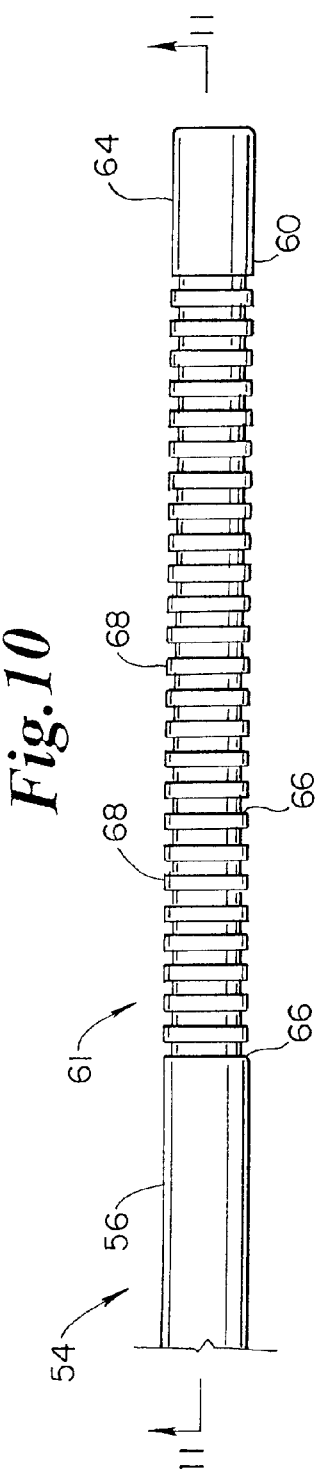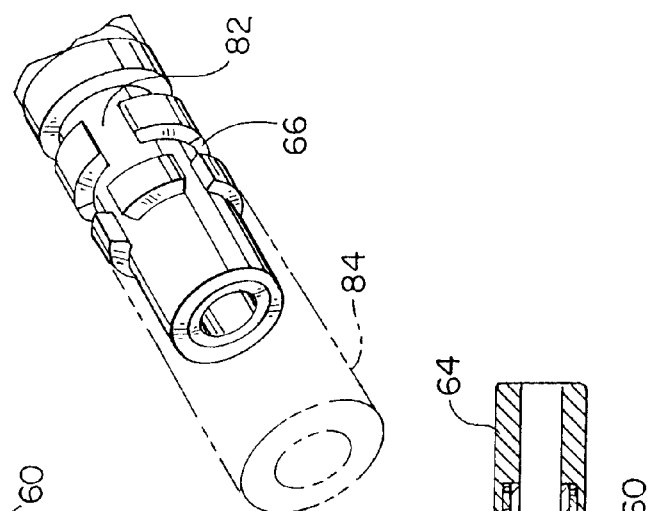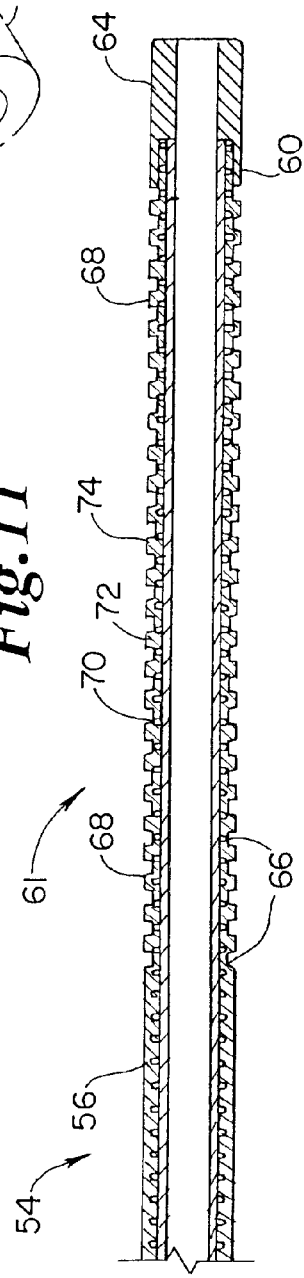

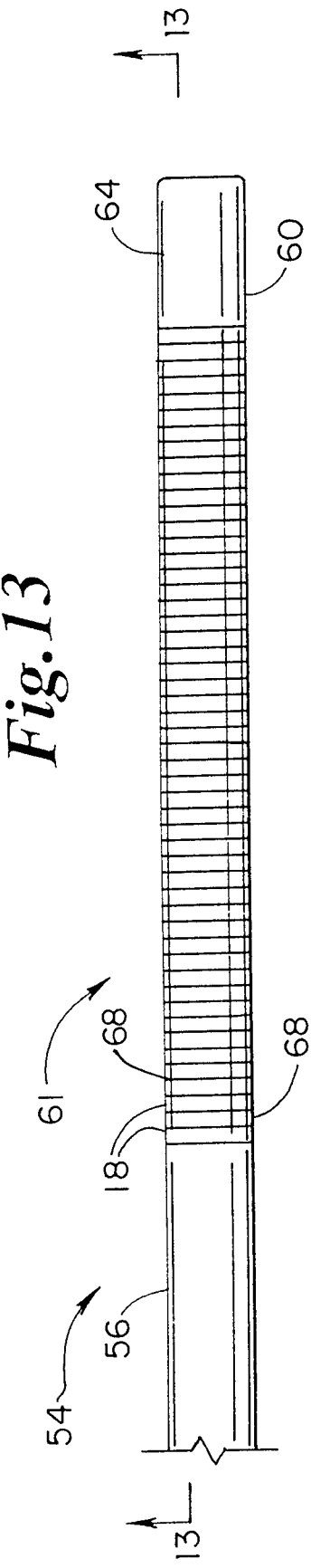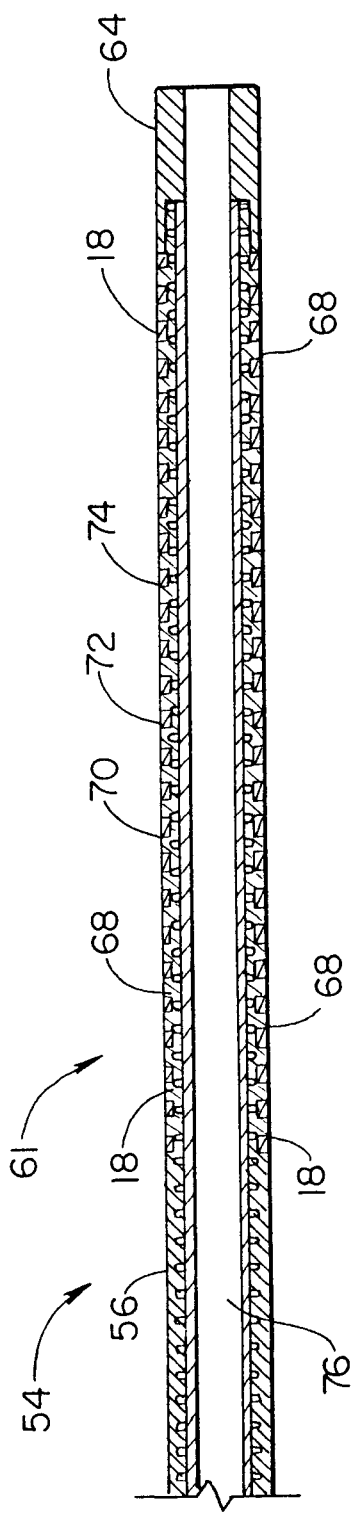

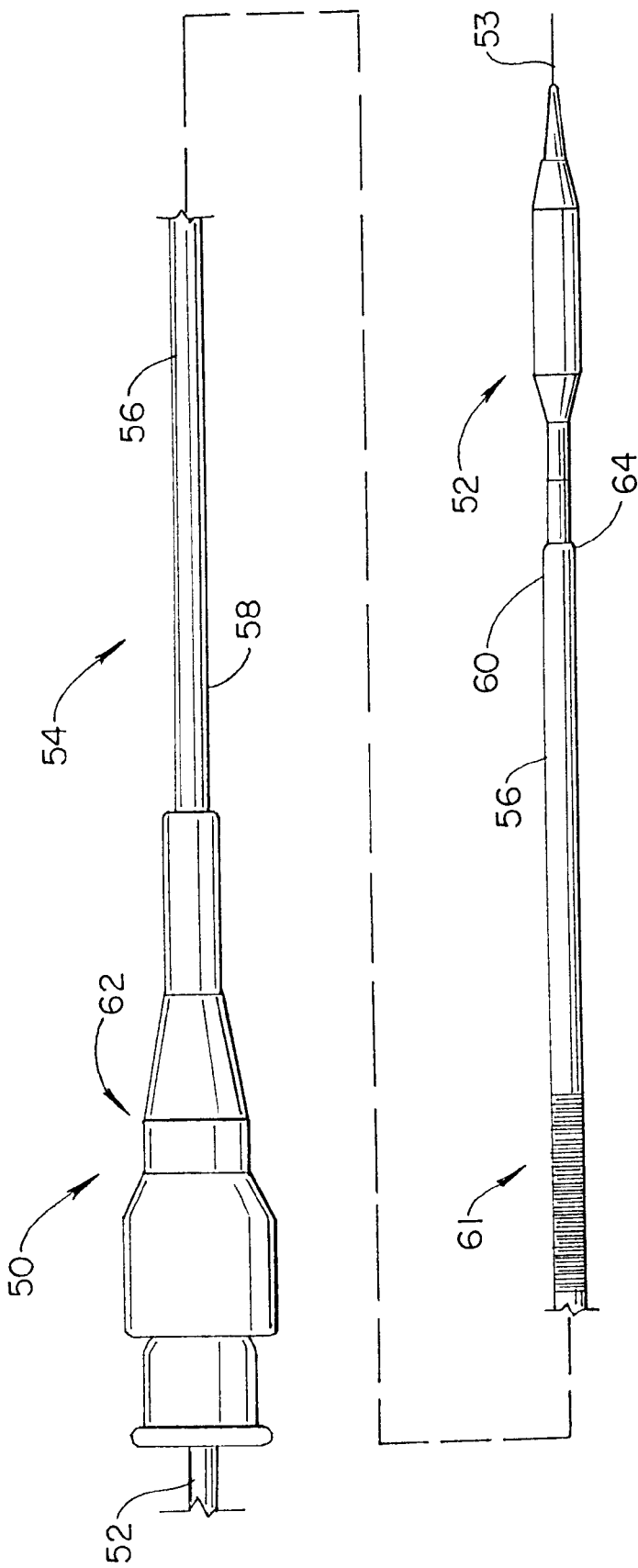

GUIDE CATHETER HAVING A PLURALITY OF FILLED DISTAL GROOVES

CROSS-REFERENCES TO CO-PENDING APPLICATIONS

This application is a continuation-in-part of U.S. patent application Ser. No. 08/195,222, filed Feb. 14, 1994, entitled "Elastic Guide Catheter Transition Element" to the same assignee, now U.S. Pat. No. 5,569,218.

BACKGROUND OF THE INVENTION

1. Field of the Invention

The present invention generally relates to the field of intravascular medical devices, and more specifically refers to the field of angioplasty catheters such as guiding catheters used for the placement of medical devices and radiopaque fluids within the body for treatment of vascular diseases. In particular, the present invention relates to an improved guide or diagnostic guide catheter of a braided or braidless catheter design, having a transition zone with a different flexibility than adjacent portions of the catheter shaft for improved catheter performance.

2. Description of the Prior Art

The use of intravascular catheters for the treatment of cardiovascular disease is well known in the field of medicine. The need for a greater variety of devices to treat different types of circumstances has grown tremendously as the techniques for the use of such devices has progressed.

Prior art guiding catheters are generally comprised of a shaft which is hollow, defining an inner lumen. The shaft is generally comprised of two tubes congruent to each other with a support member therebetween. A hub is connected to the proximal end of the shaft to provide a means for connecting another device such as a syringe to inject fluids, or for providing a means to direct the device in order to place it within the vessel. A tip of a desired shape is provided at the distal end of the shaft.

An example of the prior art catheters as described above is located in U.S. Pat. No. 3,416,531, issued Dec. 17, 1968 to M. L. Edwards, for CATHETER, which describes a catheter constructed with a reinforcement layer to impart torsional rigidity without impairing the flexibility of the device in bending. U.S. Pat. No. 3,485,234, issued Dec. 23, 1969, to R. C. Stevens, for TUBULAR PRODUCTS AND METHOD OF MAKING SAME, discloses placing the stainless steel braid in between a first and a second plastic extrusion. U.S. Pat. No. 5,254,107, issued Oct. 19, 1993, to P. O. Soltesz, for CATHETER HAVING BRAID REINFORCED TRANSITIONAL TIP, discloses a catheter which is constructed of a first tube, a reinforcement member placed over the first tube, and two different polymer tubes placed over the reinforcement layer to create two sections having different flexibilities. PCT publication No. WO 92/15356, published Sep. 17, 1992, to Nita et al., for CARDIOVASCULAR CATHETER HAVING DISCRETE REGIONS OF VARYING FLEXIBILITY, also teaches a catheter which has varying flexibilities along its length.

In order for the physician to place the catheter at the correct location in the vessel, the physician must apply longitudinal and rotational forces. In order for the catheter to transmit these forces from the proximal end to the distal end, the catheter must be rigid enough to push through the blood vessel, but yet flexible enough to navigate the bends in the blood vessel. The catheter must also be torsionally rigid to transmit the applied torque. To accomplish this balance between longitudinal rigidity, torsional rigidity, and flexibility, there is often a support member added to the shaft. This support member is often comprised of a metal braid or coil embedded in the shaft. This support wire is often embedded in the shaft between the two layers of tubing that comprise the shaft.

A guiding catheter is guided through the aorta over the aortic arch and down to the ostium of the vessel which is to be treated. It is preferable to have a soft tip or flexible section engage the ostium. Therefore, it is advantageous to have the proximal section be rigid to transmit the forces applied, but to have the distal end more flexible to allow for better placement of the guide catheter. Having the distal section more flexible also creates a less traumatic section to the blood vessel. The distal end of the catheter is rotated, through the transmission of torque from the proximal end, until the tip of the guiding catheter is in the desired position. With the variations of different bend shapes available on the distal ends of these devices and with variations in patient anatomy, each device may need to be torqued more or less in order to correctly place it.

One problem that has surfaced is that as more flexible distal sections are placed on these catheters, the resistance to guide catheter back-out is reduced. Guide catheter back-out is when the guide disengages from its preferred positioning, thereby creating the need for the physician to reposition the guiding catheter. Many different guide catheter curve shapes have been designed to overcome this problem, with each giving different levels of support. However, as the flexibility of the distal most section is reduced, the tendency for back-out again increases.

It is possible to construct a device that is very rigid to obtain the correct amount of back-out support. However, the resulting device would be very traumatic to the patient's arteries due to its rigidity. Similarly, it is possible to construct a very flexible device to limit the trauma the device imparts to the blood vessels. However, the device then becomes too flexible and does not provide any back-out support.

Another problem that is seen in current devices is that devices are constructed such that they are equally flexible in all planes. That feature is not always desired.

SUMMARY OF THE INVENTION

The present invention overcomes the disadvantages associated with the prior art by providing a transition element in the material. The present invention allows for flexibility of a guiding catheter to be increased, while maintaining its ability to prevent guide catheter back-out. The present invention also allows for the rigidity of a guiding catheter to be increased in a discrete segment, thereby increasing the back-out resistance while maintaining the flexibility. The present invention provides a manner in which a device of varying flexibility may be made very inexpensively. The present invention also provides a manner in which differential flexibility may be imparted to a guide catheter.

In the preferred embodiment of the invention, the catheter shaft material is removed in the transition section. The outer tube of the shaft is removed down to the braid of the catheter. This is done by a grinding process. The removal of this material creates a band in which there is no material present. That band is then filled with a material having different physical properties than the material which was removed, thereby changing that section's properties.

If the filler material substituted in the band is a more flexible material, the transition section will have the flexibility of both the remaining inner tube layer, the braid, and the new outer material. It is clearly seen that while this catheter section becomes a new combination, it will still be more flexible than the sections immediately proximal and distal to it. If the filler material substituted in the band is a more rigid material, the combination of the materials in this transition section will be more rigid than the sections immediately proximal and distal to it.

In another embodiment of the present invention, the transition zone is formed by removing catheter shaft material from the catheter shaft distal portion, forming one or more annular grooves, and further forming one or more longitudinal grooves contiguous with the annular grooves and contiguous with the shaft distal end. Softer, more flexible material suitable for forming an atraumatic tip is used as the filler material. The soft filler material extends distally, extending past the transition zone and forming the atraumatic tip itself. In this manner, the transition zone and tip are formed of the same material and in the same step.

Another embodiment of the present invention includes an improved intravascular catheter for use in catheter procedures. The catheter includes a shaft having a proximal end, a distal end, and a lumen extending longitudinally therethrough. The catheter shaft includes a first layer and a second layer overlying the first layer. The improvement includes a transition zone located along the catheter shaft having a different degree of flexibility than an adjacent portion of the shaft. The transition zone includes a high density of grooves.

The grooves may be generally annular grooves. The grooves may include micro-grooves. In one embodiment, the annular grooves have a density greater than 5 grooves per inch, with preferably 5 to 50 grooves per inch.

The grooves may be located within the second layer. The grooves may be generally annular, but extending less than 360° degrees about the catheter shaft to form a bending plane.

The transition zone may be located proximal of the distal end. The catheter shaft may be curved, and the transition zone may be located along the curve of the shaft. The catheter shaft may include a primary curve, wherein the transition section is located along the primary curve.

The catheter may further include a support layer overlying the first layer. The grooves may be located within the second layer and not extend down to the support layer.

The catheter may further include material located within the grooves, having a different shore hardness than the second layer. The material may be relatively softer than the second layer. Alternatively, the material may be relatively stiffer than the second layer.

In another embodiment, the present invention is an intravascular catheter for use in catheter procedures. The catheter includes a shaft having a proximal end, a distal end, and a lumen extending longitudinally therethrough. The shaft includes a first layer with a second layer overlying the first layer.

The catheter shaft includes a first curve. The improvement includes a transition zone located along the catheter shaft first curve having a different degree of flexibility than an adjacent portion of the shaft. The second layer within the transition zone has a high density of surface contours located therein.

The surface contours may be micro-contours. The surface contours may include a plurality of generally annular grooves. The catheter may further include material located within the surface contours having a different shore hardness relative to the second layer. The material may be softer relative to the second layer. Alternatively, the material may be stiffer relative to the second layer.

The catheter may include a second curve along its shaft, and a second transition zone may be located along the second curve. The catheter may further include material located within the surface contours of the second transition zone, having a different shore hardness relative to the second layer. The catheter may further include material located within the surface contours of the transition zone located along the first curve, having a greater shore hardness rating relative to the material located within the second transition zone located along the second curve.

The present invention includes a method of manufacturing a catheter for use in intravascular catheter procedures. The method includes providing a mandrel and forming a first layer over the mandrel. A second layer is overlayed or coupled to the first layer. A portion of the second layer is removed to form a high density of grooves in the surface of the second layer.

The portion of the second layer may be removed using an abrasion process. The grooves may be generally annular grooves. The abrasion process may further include the steps of rotating the catheter about its longitudinal axis. A grinding wheel having a pattern corresponding to the generally annular grooves is rotated. The catheter is moved into the grinding wheel to a desired depth. The grooves may be V-shaped.

The grooves may be micro-grooves. The density of the grooves may be greater than 5 grooves per inch, with 5 to 50 grooves per inch preferred. The grooves may be filled with a material having a different hardness rating relative to the second layer. The material may be softer relative to the second layer. Alternatively, the material may be harder relative to the second layer. The method may further include the step of grinding the catheter to a uniform outside diameter.

BRIEF DESCRIPTION OF THE DRAWINGS

The invention will be further described with reference to the accompanying drawings where like numbers refer to like parts in several views and wherein:

FIG. 1 is a plan view showing a section of the catheter shaft;

FIG. 2 is another plan view of the catheter shaft with a length of the shaft ground down to create a band;

FIG. 3 is a plan view of FIG. 2 after the filler material has been added;

FIG. 4 is a perspective view of the catheter shaft of FIG. 3;

FIG. 5 is one embodiment of the present invention;

FIG. 10 is a partial enlarged perspective view showing the transition zone along the catheter shaft;

FIG. 11 is a longitudinal cross section of FIG. 10 taken along line 11—11;

FIG. 12 is an enlarged perspective view of an embodiment wherein the transition zone includes annular and longitudinal grooves and is contiguous with the catheter distal tip;

FIG. 13 is an enlarged perspective view of yet another embodiment of the transition zone located along the catheter shaft;

FIG. 14 is a longitudinal cross section of FIG. 13 along line 13—13;

FIG. 15 is a perspective view of a guide catheter showing an application of the present invention;

DETAILED DESCRIPTION OF THE PREFERRED EMBODIMENTS

Figure 6:
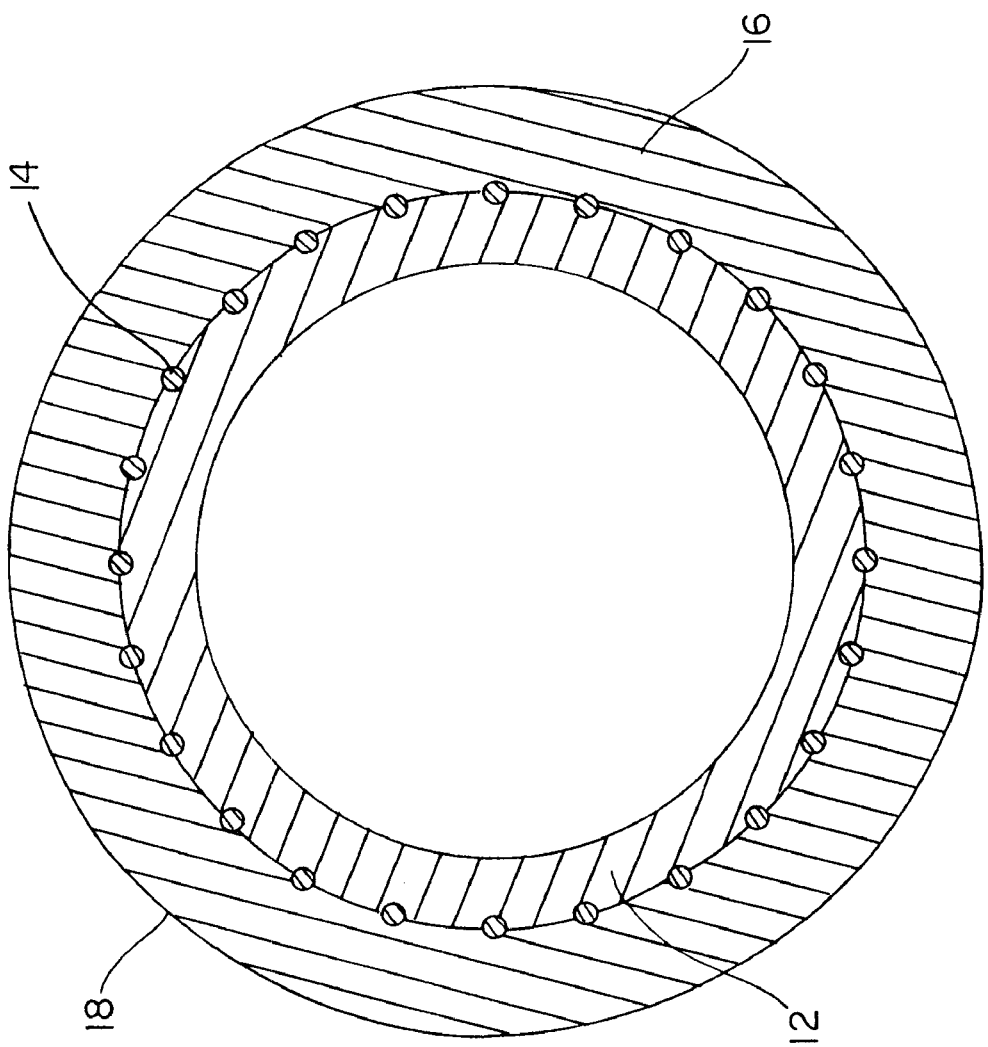
FIG. 6 is a cross section of FIG. 3 along line 6—6.

FIG. 1 shows a section of a catheter 10 which is preferably a guiding catheter. Catheter shaft 11 is comprised of an inner tube 12 which is surrounded by a support member 14. Support member 14 is then surrounded by an outer tube 16. Inner tube 12 is represented in FIG. 1 by dashed lines and the support member 14 is represented by a dashed line.

In the preferred embodiment, inner tube 12 is a thin walled PTFE (polytetrafluoroethylene) tube. This creates a smooth, friction-free surface for the passage of other devices through the inner tube. Support member 14 is a 304 stainless steel wire, wound in a braided pattern around inner tube 12. Alternatively, support member 14 could also be comprised of polymer fibers. Outer tube 16 is a polymer jacket which is placed through an extrusion process onto combined layers of inner tube 12 and support member 14. Preferably, outer tube 16 is comprised of PEBAX®, a polyether block amide (PEBA) available from ATOMCHEM POLYMERS, Birdsboro, Pa. FIG. 6 shows a cross section of this construction.

FIG. 2 is a drawing of a portion of catheter 10. Catheter shaft 11 is shown having a section ground or abraded away to create a band 15 in which no material exists. As shown in FIG. 2, outer tube 16 is removed to expose the support member 14, and to create a band 15 which will be filled later with a different material.

In the preferred embodiment, outer tube 16 is removed through an abrasion process. Specifically, the section in which the band 15 to be created is brought in contact with a grinding wheel. Catheter shaft 11 is then rotated 360 degrees to remove material circumferentially around the device. The grinding wheel is slowly advanced to increase the depth of the cut until the support member 14 is exposed. Although abrasion is the preferred mode of processing, the band 15 can be created in many different ways, some of which include alternate extrusion methods, cutting, and thermal processing.

FIG. 3 is a plan view of the device depicted in FIG. 2 after the different material, filler material 18, has been placed in the band 15 to create the transition section 22. Filler material 18 is an element which has different physical properties than the outer tube 16. For example, if the catheter shaft 11 is comprised of a flexible polymer, the filler material 18 may be either a rigid polymer, a rigid metal, or an even more flexible polymer. Likewise, if the catheter shaft 11 is comprised of a rigid polymer, the filler material 18 may be a more flexible polymer material.

Filler material 18 is preferably a circular polymer tube with a diameter equal to the diameter of the band 15 and a length equal to the length of the band. The filler material 18 is cut longitudinally to allow it to be placed over the catheter shaft 11 and onto the band 15. A processing sleeve is then loaded over both the catheter shaft and the band. The entire transition section 22 is then subjected to a heating source to cause the materials to flow together. The processing sleeve allows for a smooth outer surface following thermal processing.

In the preferred embodiment, the outer tube 16 is comprised of PEBAX having a durometer of 67 D. Although 67 D is preferred, the outer tube could be on the order of 40–72 D. The filler material 18 is also comprised of PEBAX, but has a durometer of 25 D. Although 25 D is preferred, the outer tube could be on the order of 5–72 D. In the preferred embodiment, the band 15 length is in the order of 0.1 to 0.75 inches. The thickness of the band 15 varies with the amount of outer tube 16 material which is removed. For example, in an 8F guiding catheter, the diameter of the outer tube is in the order of 0.102–0.106 inches. After the material is removed, the diameter of the band 15 is on the order of 0.092–0.096 inches. The diameter of the catheter shaft 11, or outer tube 16, also varies with the desired end use for the product. A guiding catheter may be on the order of five to ten French, while a balloon angioplasty catheter will be on the order of two to five French.

FIG. 4 shows the perspective view of the device when completed. Band 15 is replaced with filler material 18 in a circumferential pattern around the catheter shaft 11.

FIG. 5 shows a specific application of this invention in the area of guiding catheters. Guiding catheter 40 is comprised of a catheter shaft 11 which is constructed as described above. Connected to the proximal end of the catheter shaft 11 is a hub 30 and strain relief 32. The connection of these elements allows the physician to connect other devices to the guiding catheter 40 and to manipulate the device through the application of longitudinal or rotational forces. Connected to the distal end of the catheter shaft 11 is a distal tip 20. Distal tip 20 generally consists of a softer, more flexible polymer which is connected to the catheter shaft 11 through a thermal process. In the preferred embodiment, distal tip 20 is comprised of a PEBAX polymer tube having a durometer of 35–40 D. Distal tip 20 generally does not contain either the inner tube 12 or the support member 14. However, it is possible for these elements to be present in a portion of the distal tip 20.

The most distal section of the guiding catheter 40 is formed to correspond to a desired geometrical shape. This shape is determined by the specific anatomy of the patient, and the amount of guide catheter back-out support that is needed for the procedure. Generally, the guiding catheter has at least two bends at the distal end of the catheter shaft 11. These are the primary curve 26 and the secondary curve 28. These curves assist the physician in the placement of the device for treatment of the vessels.

In order to simultaneously maximize the amount of guide catheter back-out support and the flexibility of the distal end of the device, the present invention can be used. The present invention utilizes a catheter shaft which is relatively rigid to provide for good guide catheter back-out support, and combines that with a filler material 18 which is relatively flexible. Therefore, a transition section 22 is created which is more flexible to allow for easier and less traumatic guide catheter placement. Flexible transition sections 22 can be located where tight radiuses are created due to the shape of the guide catheter to allow larger devices to pass through the curve with greater ease. The transition sections 22 act as elastic joints which better accommodate devices by allowing the shaft to straighten. In this embodiment, the transition sections 22 are created at the primary curve 26 or the secondary curve 28. This placement of the transition sections 22 provides the benefits of a flexible distal section and the benefits of a rigid distal section simultaneously. The transition sections 22 can be located strategically within the guide catheter shaft. Ideal locations include: a flexible transition section 22 at the primary curve radius to allow safer deep seating of the guide, flexible transition sections 22 at radius locations within the curve style to improve ease of device passage as it remains coaxial within the vessel lumen and a rigid transition section 22 at the secondary curve to provide maximum back-out support.

Transition sections 22 can be applied to the main shaft in as many locations as needed. Because the support member 14 and the inner tube 12 are continuous through the transition section 22, a stronger bond is created. This is a key advantage over butt joints as described and used in the prior art. Most catheter shafts are made to be rigid the entire length of the catheter shaft to ensure that correct stiffness occurs at the desired locations. The catheter shaft does not need to be rigid the entire length to provide back-out support. The present invention allows for the rigidity or flexibility to be added only where it is needed.

In an alternative embodiment of the present invention, it is desired to start with a more flexible catheter shaft 11 and create zones of rigidity through the use of the present invention. Bands 15 can be created in the catheter shaft 11 and filled with a more rigid filler material 18, thereby creating a transition section 22 which is more rigid.

Figure 7:
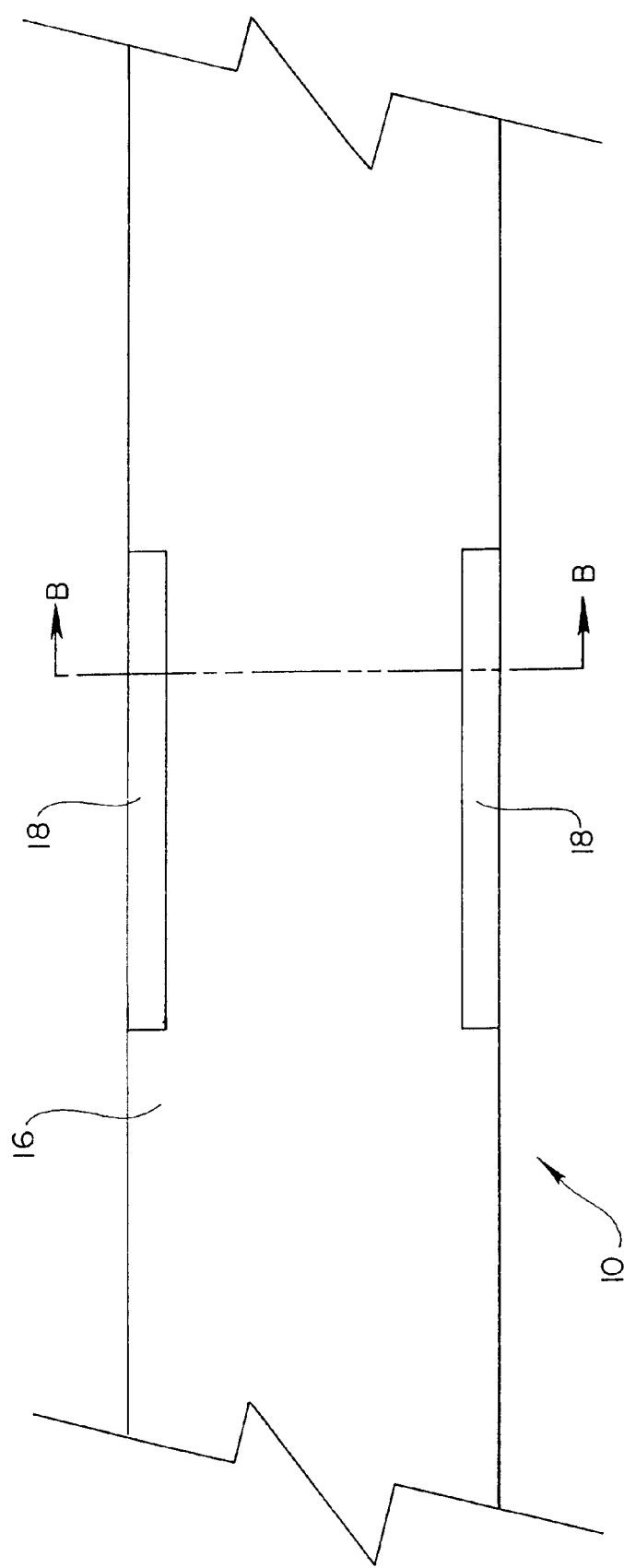
FIG. 7 is another embodiment of the present invention.
Figure 8:
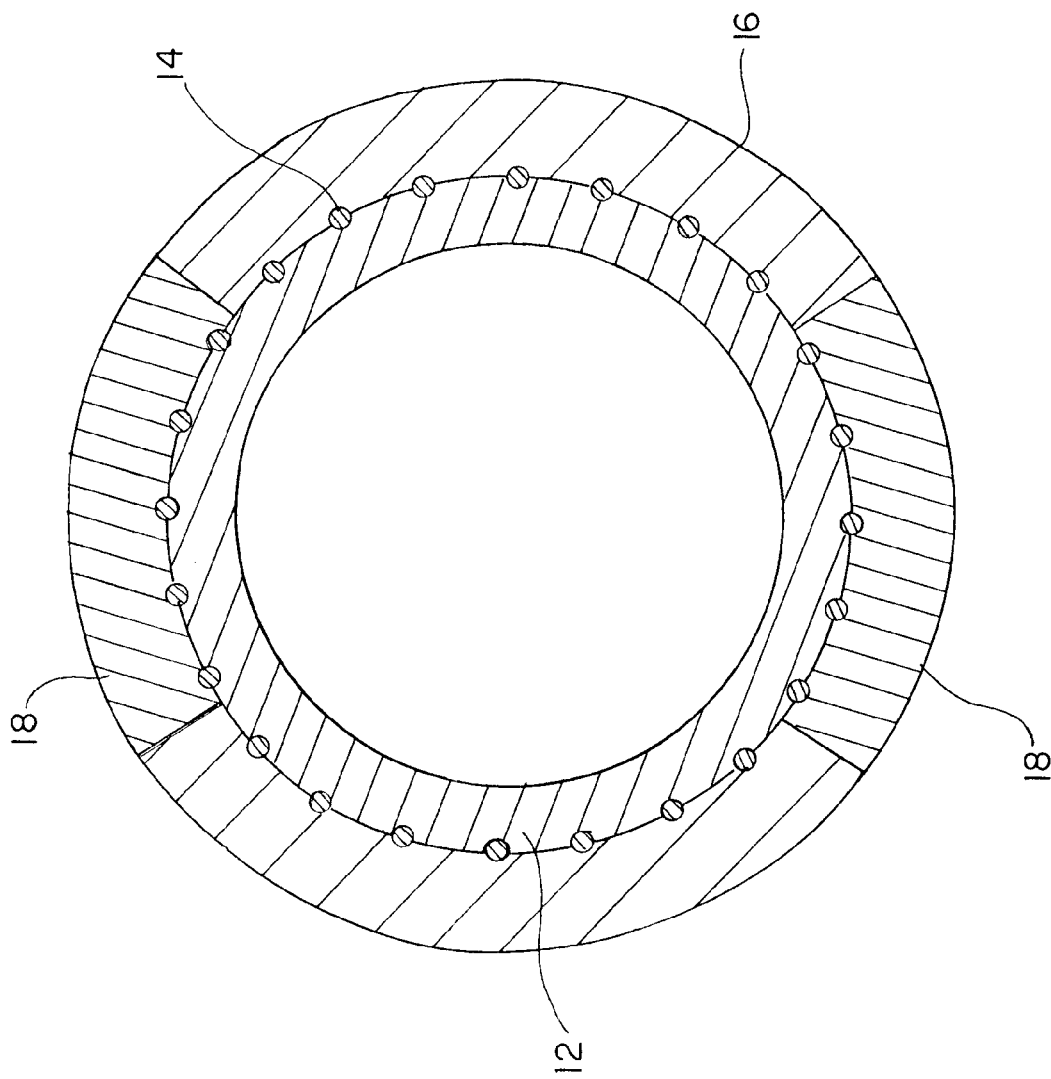
FIG. 8 is a cross section of FIG. 7 along line 8—8.

FIGS. 7 and 8 represent another embodiment in which it is desired to create bending planes within the catheter shaft 11. This also can be accomplished through the use of the present invention. The catheter can be processed as described above, but instead of grinding the band 15 in a 360 degree manner, opposing sides of the catheter shaft 11 may be ground down and then filled with a more flexible filler material 18 to create a plane in which the transition element may bend. Alternatively, a flexible catheter shaft 11 can be ground down on opposing sides and then filled with a more rigid filler material 18, to create planes in which the catheter may not bend.

In another embodiment of the present invention, the filler material 18 may be a composite or a blend of two different substances. Specifically, it may be comprised of a polymer tube which has a spring coil embedded therein to impart different flexibility in that section. It may also be comprised of two or more polymer sections that have physical properties that are different from each other and from the catheter shaft 11.

Figure 9:
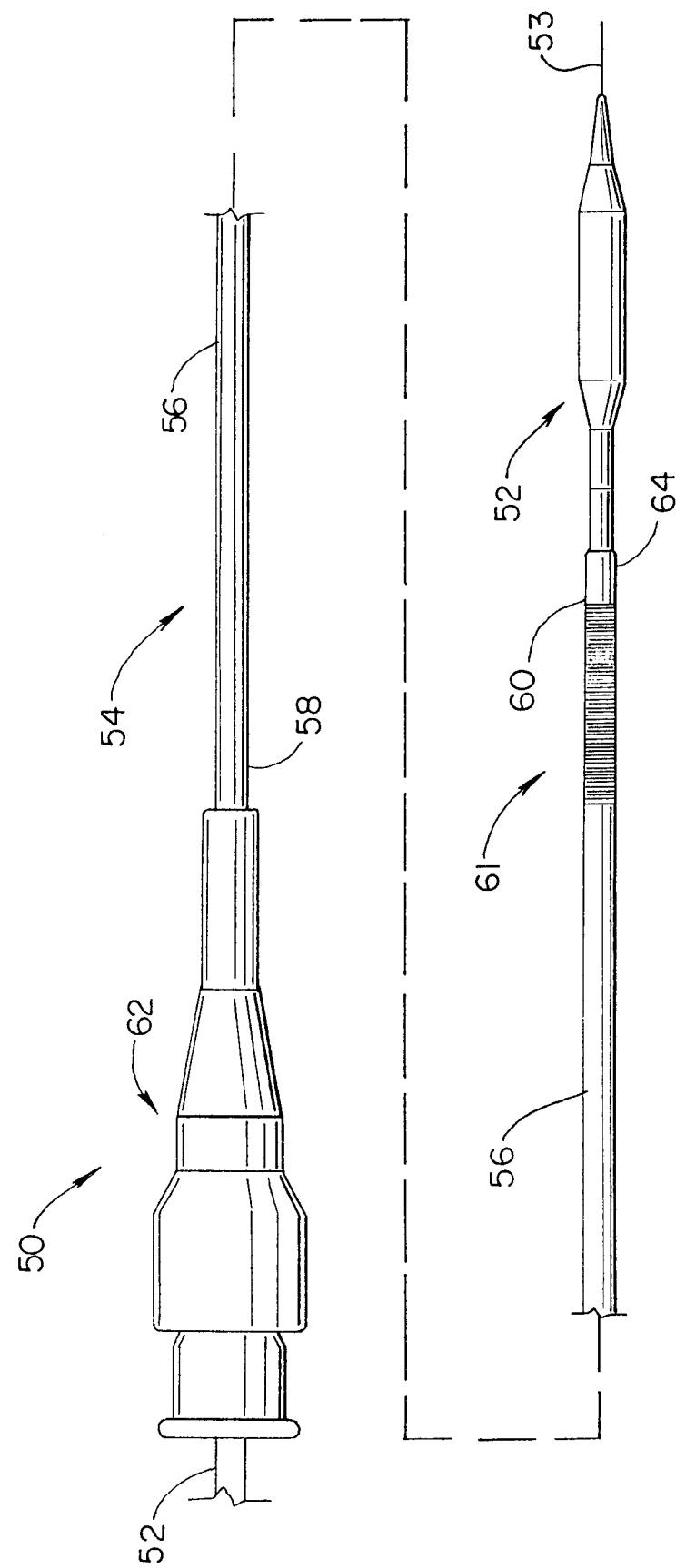
FIG. 9 is a plan view of another embodiment of the present invention, including a transition zone located along the catheter shaft.

Yet another embodiment of the present invention is shown in FIG. 9. FIG. 9 shows a catheter assembly generally at 50, which includes a dilatation catheter 52 positioned over guide wire 53, within guide catheter 54. Guide catheter 54 can be similar to the catheter 10 as previously described herein.

Catheter 54 includes a shaft 56 having a proximal end 58 and a distal end 60. Operably connected to the proximal end 58 of the shaft 56 is a hub assembly 62. Operably connected to the distal end 60 of the shaft 56 is a soft tip 64. Located with respect to the distal end 60 is transition zone 61.

FIG. 10 is a partial enlarged perspective view of transition zone 61. Transition zone 61 can be similar to transition section 22 as previously described herein. With transition zone 61, the performance of catheter 54 is changed using mechanical properties (such as the use of surface contours or annular grooves shown), rather than changing catheter materials. Transition zone 61 is used to change the flexibility of guide catheter 54 at desired locations along shaft 56, improving catheter performance. U.S. Pat. No. 5,358,493 to Schweich, Jr. et al. disclose a catheter shaft having a proximal section, an intermediate section, and a distal section having different degrees of flexibility, which is herein incorporated by reference.

In one embodiment, transition zone 61 includes a plurality of alternating sections, consisting of annular grooves 66 and raised portions (or rings) 68. The alternating grooves 66 and raised portions 68 extend radially about the catheter shaft 56. With this embodiment, the transition zone 61 is more flexible relative to the adjacent portions of shaft 56, even though transition zone 61 and shaft 56 may be constructed of similar materials.

Referring to FIG. 11, a longitudinal cross-sectional view of guide catheter 54 is shown. Guide catheter 54 is multi-layered, and includes an inner layer 70, a support layer 72, and an outer layer 74. The inner layer 70 is in the form of a tubular member defining a lumen 76 extending longitudinally therethrough. Support layer 72 is formed over the inner layer 70 and includes helically braided strands. The strands may be metallic or non-metallic and may be formed over inner layer 70 or partially embedded within the inner layer 70.

Outer layer 74 is formed over support layer 72 and inner layer 70. Outer layer 74 is formed of a material which has a similar stiffness or durometer relative to inner layer 70. Alternatively, it is recognized that outer layer 74 may be formed of a material which has a different stiffness or durometer relative to inner layer 70. Along transition zone 61, portions of outer layer 74 are removed to form grooves 66 and raised portions 68. With this construction, transition zone 61 is more flexible relative to the remaining portions of catheter shaft 56.

In one embodiment, inner layer 70 is formed of an extruded polymeric material, such as polyether block amide, having a durometer between 60 D and 72 D. Support layer 72 is formed of braided stainless steel strands. Outer layer 74 is formed of an extruded Nylon, also having a durometer between 60 and 72 D.

In one embodiment (shown in FIGS. 10 and 11), transitional zone 61 is approximately 0.5 inches long and located proximal to the distal end 60 of shaft 56. The transition zone 61 is formed of a "micro-groove" construction. The transition zone 61 includes a high density of grooves.

In one preferred embodiment, the density is greater than 5 grooves per inch, with each groove 66 and raised portion 68 being approximately 0.010 inches wide and 0.005 inches deep for an 8-French diameter device. The micro-groove construction allows flexibility to be added to guide catheter 54 at desired locations along its shaft 56, or along the entire length of the guide catheter shaft 56, without the use of bonded catheter segments. The micro-groove construction allows for improved catheter performance within a patient's vascular system.

In one preferred embodiment, grooves 66 extend into a portion of outer layer 74, but do not extend down to support layer 72. The "micro-groove" construction of the present invention allows the flexibility of catheter shaft 56 to be changed at desired areas or "transition zones" along the catheter shaft 56 without sacrificing the structural integrity of the catheter shaft through bonding, fusing, or similar procedures. For braided catheter construction, a continuous support layer 72 extends through the extension of catheter shaft 56 proximal of transition zone 61, through transition zone 61, and through the portion of the catheter shaft which is distal of transition zone 61.

Figure 11A:
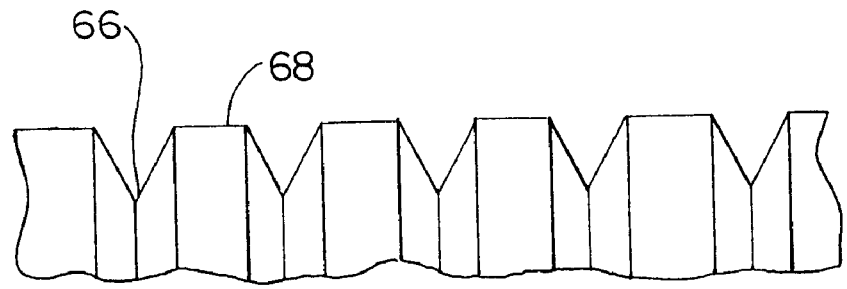
FIG. 11A is a partial view of the longitudinal cross section of FIG. 11 depicting an alternative V-shaped annular groove.
Figure 11B:
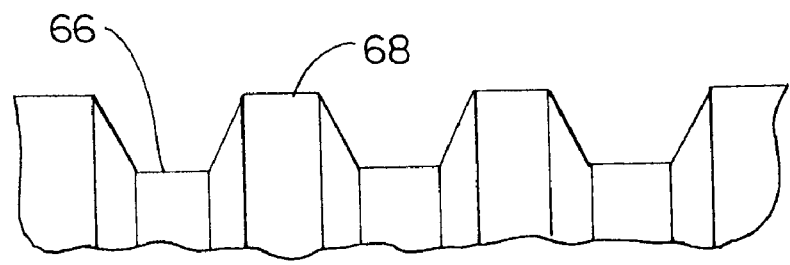
FIG. 11B is a partial view of the longitudinal cross section of FIG. 11 depicting a second alternative annular groove configuration.
Figure 11C:
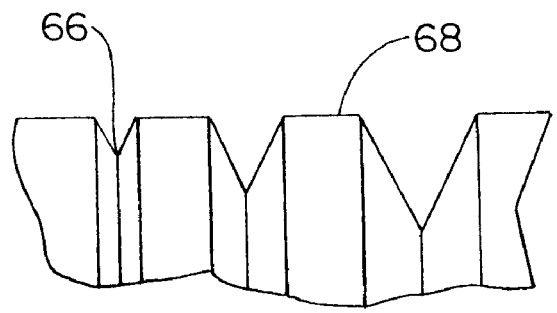
FIG. 11C is a partial view of the longitudinal cross section of FIG. 11 depicting annular grooves of varying depth and width along the longitudinal length of the catheter.

As depicted in FIG. 11, each of the microgrooves has a generally rectangular cross section. FIGS. 11A, 11B and 11C depict alternative cross sections for the microgrooves which allow further variability in the flexibility of the micro-grooved section of the shaft. FIG. 11A depicts multiple V-shaped microgrooves 66 separated by generally flat raised portions 68. The V-shaped groove allows for varying the flexibility of the shaft radial within a given longitudinal section. As depicted in FIG. 11B, the microgroove 66 may be of a generally trapezoidal shape. Finally, the width and depth of the microgrooves 66 may be varied along a given longitudinal section of a catheter. This allows variation in flexibility over such section from groove to groove.

The micro-groove construction provides an economical, yet effective method for improving catheter performance. By using micro-groove construction within transition zone 61, changes in catheter material are not necessary, nor sacrifices in structural integrity, for changing the flexibility along desired locations of catheter shaft 56. With micro-groove construction, additional filler materials are not necessary within transition zone 61. The micro-groove construction limits the patient's exposure to catheter procedure problems, such as embolism and ischemia, while providing improved catheter performance during the catheter procedure.

It is recognized that inner layer 70, support layer 72, and outer layer 74 may be formed of other materials. In one embodiment, the inner layer 70 is formed of polytetrafluoroethylene having a durometer between 60 and 72 D, and outer layer 74 is formed of polyether block amide having a durometer between 60 D and 72 D. It is recognized that guide catheter 54 may be a braidless guide catheter, without support layer 72.

Transition zone 61 has a different flexibility than the portion of catheter shaft 56 proximal of transition section 61 and the portion of catheter shaft 56 distal of transition zone 61. In one embodiment, transition zone 61 is relatively more flexible than the portion of catheter shaft 56 proximal of transition zone 61 and the portion of catheter shaft 56 distal of transition zone 61. In another application, transition zone 61 is relatively more stiff than the portion of catheter shaft 56 which is proximal of transition zone 61 and the portion of catheter shaft 56 which is distal of transition zone 61.

Referring to FIG. 13, guide catheter 54 may further include filler material 18 located within grooves 66. Referring also to FIG. 14, guide catheter 54 having lumen 76 therethrough illustrates filler material 18 is located within grooves 66 such that guide catheter 54 has a generally uniform outside diameter. Filler material 18 is a material having a durometer which is softer relative to the durometer of inner layer 70 and outer layer 74. In one embodiment, inner layer 70 is formed of polyether block amide having a durometer between 60 D and 72 D, outer layer 74 is formed of Nylon having a durometer between 60 D and 72 D, and filler material 18 is formed of a relatively softer polyether block amide having a durometer between 75 A and 40 D. Alternatively, it is recognized that filler material 18 may be formed of other soft, flexible materials, which includes flexible adhesives, such as urethane oligomer/methacrylate monomer blends which can be ultraviolet curable such as Dymax 138-M std. A preferred viscosity is about 350 cps. with a 40 D durometer.

Since filler material 18 has a durometer which is softer relative to outer layer 74 and inner layer 70, transition zone 22 is more flexible relative to the remaining portion of the guide catheter 54 shaft 56. Additionally, filler material 18 allows transition zone 61 and guide catheter 54 to have a smooth, generally uniform outside diameter. By using transition zone 61 at desired locations along shaft 56, catheter performance is improved by creating and controlling catheter flexibility in sections independent of the shaft stiffness.

Alternatively, if it is desired for transition zone 61 to be stiffer (or less flexible) relative to inner layer 70 and outer layer 74, filler material 18 may consist of a material having a higher durometer relative to inner layer 70 and/or outer layer 74. In one embodiment, filler material 18 is formed of polyether block amide or nylon, having a durometer between 70 D and 80 D.

Now referring to FIG. 12, an embodiment of the present invention is illustrated, wherein the transition zone includes one or more annular groove 66 contiguous with a plurality of longitudinal grooves 82 contiguous with a catheter distal tip 84. In this embodiment, the catheter distal tip 84 may be made of the same filler material as that filling the annular groove 66 and longitudinal groove 82. By using the same material in annular grooves 66, longitudinal grooves 82, and catheter distal tip 84, the tip 84 may be made in the same step as the step filling the grooves 66 and 82. This creates a transition zone between catheter shaft 56 and catheter distal tip 84, as well as reducing manufacturing cost by eliminating a separate additional step for tip creation. The invention disclosed by the embodiment of FIG. 12 is discussed further in co-pending U.S. patent application Ser. No. 08/703,641, filed Aug. 27, 1996, entitled "Insert Molded Catheter Tip" to the same assignee.

Referring to FIG. 15, it is recognized that transition zone 61 may be located at different locations along catheter shaft 56 to improve catheter performance as desired for specific catheter procedures. In each application, the section of catheter shaft proximal to transition zone 61 and the portion of catheter shaft distal of transition zone 61 has a different degree of flexibility than transition zone 61. In one embodiment, transition zone 61 is relatively more flexible than the catheter shaft section proximal to transition zone 61 and/or relatively more flexible than the portion of catheter shaft 56 distal of transition zone 61. Alternatively, transition zone 61 may be relatively stiffer than the portion of catheter shaft which is proximal to transition zone 61 and/or relatively stiffer than the portion of the catheter shaft which is distal to the transition zone 61.

Figure 16:
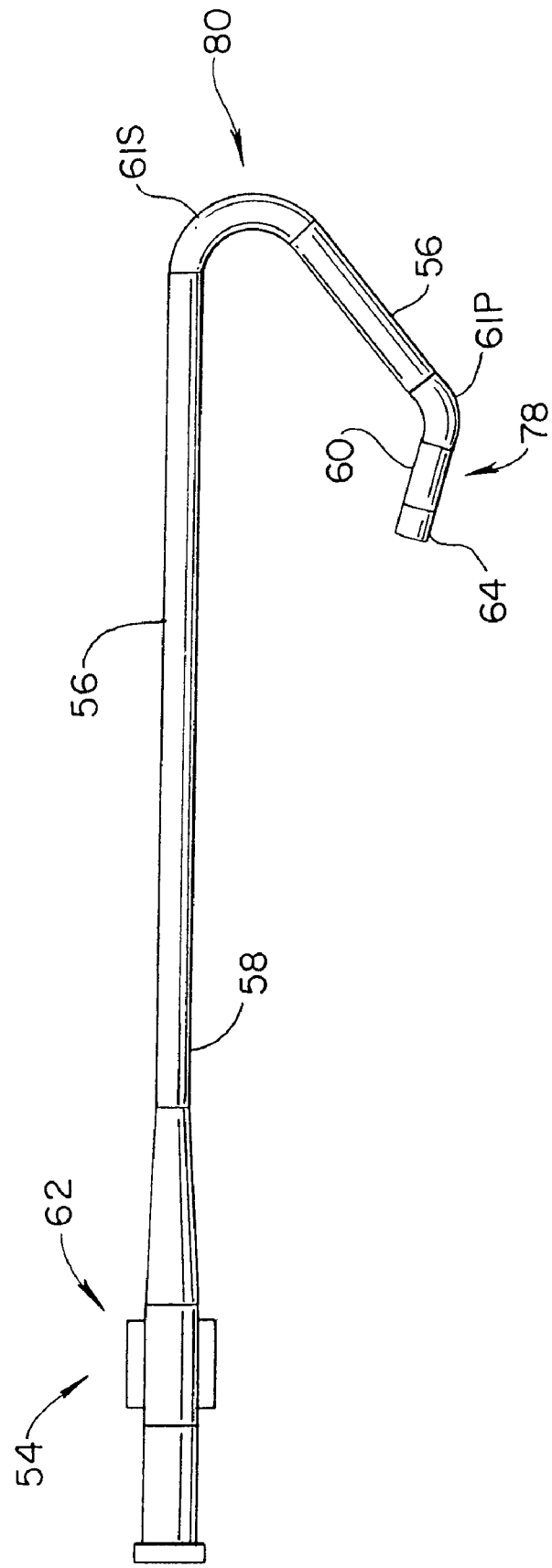
FIG. 16 is a perspective view of a guide catheter showing another application of the present invention.

Referring to FIG. 16, one application of the present invention is shown. Guide catheter 54 is curved to a desired geometrical shape for accessing a desired anatomical location during a catheter procedure. As shown, guide catheter 54 includes a primary curve 78 and a secondary curve 80. A transition zone 61 (labeled 61P) is located at the primary curve 78 and a transition zone 61 (labeled 61S) is located at the secondary curve 80.

In this embodiment, it is desirable to have a relatively flexible transition zone 61 located at primary curve 78 to aid in seating guide catheter 54 tip 64 within the ostium of the coronary receiving treatment. Therefore, the primary curve transition zone 61 is contoured, and may include "microgrooves" having grooves 66 and raised portions 68 as shown in FIGS. 10 and 11. Transition zone 61 may further include filler material 18 located within grooves 66, as shown in FIGS. 13 and 14, wherein the filler material 18 is of a softer durometer than inner layer 70 and/or outer layer 74.

It is also desirable that transition zone 61 located at the secondary curve 80 be stiffer relative to the remaining portions of guide catheter shaft 56 for improving backout support of guide catheter 54 during coronary treatment. Secondary curve transition zone 61 includes filler material 18 located within grooves 66. Filler material 18 is a material having a durometer which is stiffer relative to the durometer of the material forming inner layer 70 and outer layer 74. This construction increases the stiffness of transition zone 61 located at secondary curve 80 relative to the remaining portion of the guide catheter 56.

Figure 17:
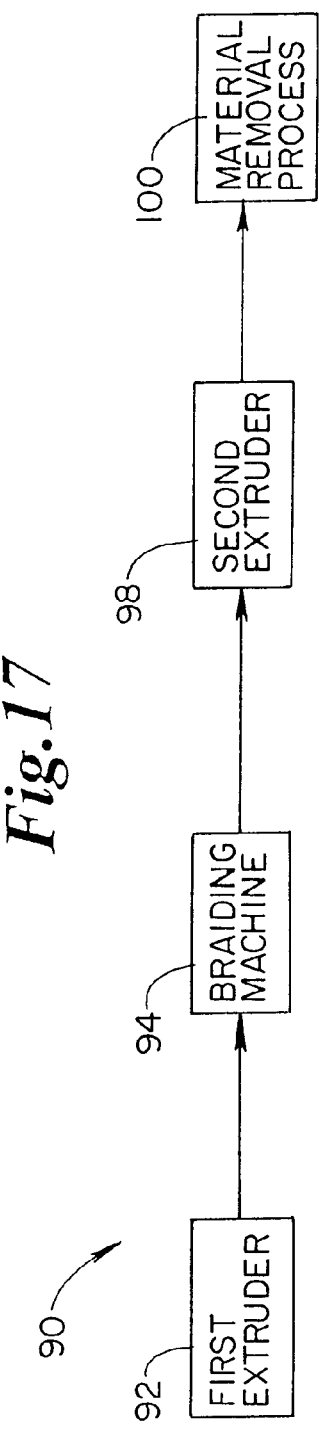
FIG. 17 is a schematic block diagram showing one method of manufacturing a catheter in accordance with the present invention.

Referring to FIG. 17, a process of manufacturing catheter 54 having transition zone 22 is shown generally in schematic form at 90. A mandrel (not shown) passes through a first extruder 92 for extruding inner layer 70. After cooling, the coated mandrel is next passed through braiding machine 94 for braiding support layer 72 over inner layer 70. The braided catheter construction may pass through a heated dye (not shown) for partially embedding the support layer 72 within the inner layer 70. Next, guide catheter 54 is passed through second extruder 98 for extruding the outer layer 74 over the support layer 72 and inner layer 70. As previously described herein, the extruded inner layer 70 and outer layer 74 are formed of materials having a generally similar durometer. In one embodiment, extruded inner layer 70 and extruded outer layer 74 have a relatively stiff durometer in the range between 60 D and 72 D to maximize catheter response during a coronary procedure.

Guide catheter 54 passes through material removal process 100 to form transition zone 61 having a contoured, grooved (or micro-grooved) construction. In one embodiment, the material removal process 100 is an abrasion process similar to that previously described herein. In one embodiment, the abrasion process uses a grinding wheel having notches corresponding with the desired transition zone 61 pattern. The grinding wheel is rotated, and positioned adjacent the catheter 54 shaft which is simultaneously rotated. The rotating catheter shaft is moved slowly into the rotating grinding wheel for grinding grooves within the catheter 54 shaft to a desired depth, forming the grooved construction of transition zone 61. In one preferred embodiment, the material removal process removes a portion of outer layer 74, but does not remove material down to support layer 72. Alternatively, it is recognized that the material removal process may remove material from the outer layer 74 at a depth down to (and exposing) support layer 72.

The rotating catheter shaft is moved away from the rotating grinding wheel, and may be moved longitudinally along its rotating axis relative to the grinding wheel for forming larger areas of transition zone 61, or multiple transition sections 22. Catheter 54 may be provided with a grooved outer layer 74 at desired locations, or along the entire guide catheter 54 shaft 56.

Figure 18:
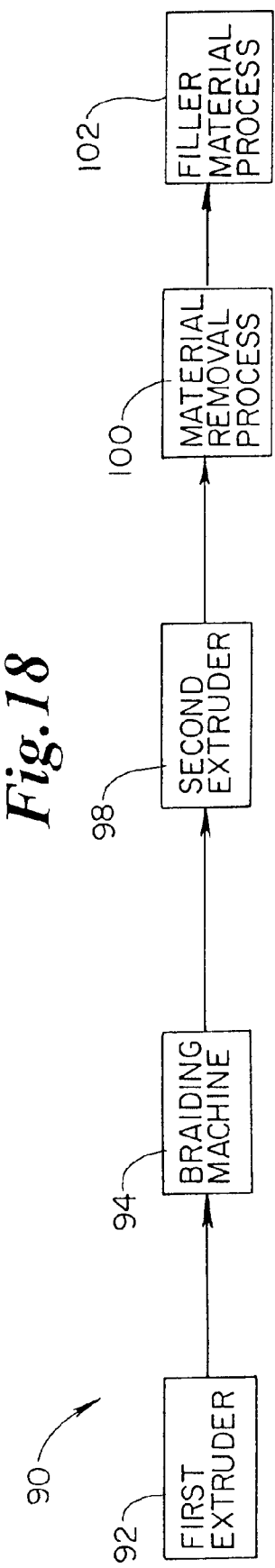
FIG. 18 is a schematic block diagram showing yet another method of manufacturing the present invention.

Referring to FIG. 18, the manufacturing process 90 may further include a filler material process 102 for positioning filler material 18 within grooves 66. The filler material 18 may be of a greater or lower durometer than the material forming inner layer 70 and/or outer layer 74 to form relatively stiffer or relatively more flexible transition zone 61 as desired.

In one embodiment, the filler material process 102 includes placing a sleeve over the transition zone 61 similar to the process previously described herein. The sleeve and the transition zone 61 are exposed to a heating source to cause the materials to flow together, resulting in filler material 18 being located within groove 66. The catheter shaft may then be subjected to a secondary grinding process to provide the guide catheter 54 with a uniform outer diameter through transition zone 61.

In another embodiment, the filler material process may include an insert molding process. The portion of guide catheter 54 having transition zone 61 may be placed into an insert mold. The desired filler material 18 is then injected into the mold and the mold is cooled. The transition zone 61 is then removed from the mold and subjected to a secondary grinding process providing a constant outside diameter to the guide catheter shaft.

Alternatively, filler material 18 may be a flexible adhesive, as previously described herein. The flexible adhesive is applied to transition zone 61, filling in grooves 66. The excess adhesive is wiped away, leaving the catheter shaft 56 with a generally uniform outside diameter.

It is recognized that transition zones 61 may be located along catheter shaft 56 to create "bending planes" as previously described herein. In this application, the grooves, contours, or generally annular "micro-grooves" do not extend 360° about the catheter shaft. The grooves are located on opposing sides of the catheter shaft 56. With this construction, the catheter more readily bends in a first plane about the grooved portions, relative to a second plane which does not include the grooved portions.

As previously described herein, the opposing sides of catheter shaft 56 may include grooves by methods as previously described herein, and then be filled with a relatively more flexible filler material 18, creating a plane in which the transition zone 61 may bend. Alternatively, the catheter shaft 56 may be ground down on opposing sides and then filled with a relatively more rigid filler material 18, to create planes in which the catheter shaft resist bending relative to the opposing side which do not include grooves.

Although the present invention is described in terms of the preferred embodiment above, it should be noted that alterations and modifications of this invention will be possible without departing from the spirit and scope of this invention.

What is claimed is:

1. In an intravascular catheter for use in catheter procedures including a shaft having a proximal end, a distal end, a longitudinal surface extending therebetween and a lumen extending longitudinally therethrough, the improvement comprising:

a transition zone located along the catheter shaft having a different degree of flexibility than an adjacent portion of the shaft, said transition zone including a plurality of grooves in said longitudinal surface, wherein a material is deposited within the grooves having a different shore hardness relative to the material of the shaft in the transition zone having said grooves.

2. The catheter of claim 1, wherein said shaft is multilayered, and includes a first, inner layer, a second layer disposed outwardly from the first layer and the grooves in said transition zone are located within the second layer.

3. The catheter of claim 2, further including a support layer between the first and second layers.

4. The catheter of claim 3, wherein the grooves are located on the outer surface of the second layer, but do not extend down to the support layer.

5. The catheter of claim 1, wherein the grooves are annular grooves.

6. The catheter of claim 1, wherein the grooves have a density greater than 5 grooves per inch.

7. The catheter of claim 1, wherein the grooves are generally annular, extending less than 360° about the catheter shaft to form a bending plane.

8. The catheter of claim 1, wherein the transition zone is located proximal of the distal end.

9. The catheter of claim 1, wherein the catheter shaft is curved, and the transition zone is located along the curve of the shaft.

10. The catheter of claim 1, wherein the catheter shaft includes a primary curve, and the transition zone is located along the primary curve.

11. The catheter of claim 1, wherein the material deposited within the grooves is relatively softer than the material of the shaft in the transition zone.

12. The catheter of claim 1, wherein the material deposited within the grooves is relatively stiffer than the material of the shaft in the transition zone.

13. In an intravascular catheter for use in catheter procedures including a shaft having a proximal end, a distal end, and a lumen extending longitudinally therethrough, wherein said shaft is multilayered, including a first, inner layer, with a second layer disposed outwardly from the first layer, the improvement comprising:

a first curve along said catheter shaft having a transition zone having a different degree of flexibility than an adjacent portion of the shaft, the second layer within the transition zone having surface contours located therein, wherein a material is deposited within the surface contours having a different shore hardness relative to the material of the second layer.

14. The catheter of claim 13, wherein the catheter includes a second curve along its shaft, and a second transition zone located along the second curve, the second layer within the second transition zone having surface contours located therein.

15. The catheter of claim 14, further comprising material located within the surface contours of the second transition zone having a different shore hardness relative to the second layer.

16. The catheter of claim 15, wherein said material located within the surface contours of the transition zone located along the first curve, has a different shore hardness rating relative to the material located within the second transition zone located along the second curve.

17. The catheter of claim 13, wherein the surface contours include a plurality of generally annular grooves.

18. The catheter of claim 13, wherein the material is relatively softer than the second layer.

19. The catheter of claim 13, wherein the material is relatively stiffer than the second layer.

20. In an intravascular catheter for use in catheter procedures including a shaft having a proximal end, a distal end portion, and lumen extending longitudinally therethrough, wherein said shaft is multilayered, and includes a first, inner layer, and a second layer disposed outwardly from the first layer, the improvement comprising:

a transition zone located along the catheter shaft having a different degree of flexibility than an adjacent proximal portion of the shaft, comprising a plurality of annular grooves and a plurality of longitudinal grooves, wherein a material is deposited within the grooves being relatively softer than the second layer, said material extending distally to form a distal tip.

21. The catheter of claim 20, wherein the transition zone is located proximal of the catheter distal tip.

* * * * *